(12) United States Patent
Wei et al.

(10) Patent No.: US 9,395,292 B2
(45) Date of Patent: Jul. 19, 2016

(54) METHOD AND APPARATUS FOR IMAGE-BASED COLOR MEASUREMENT USING A SMART PHONE

(71) Applicant: Datacolor Holding AG, Lucerne (CH)

(72) Inventors: Hong Wei, Princeton, NJ (US); Taeyoung Park, West Windsor Township, NJ (US); Albertus Busch, Skillman, NJ (US)

(73) Assignee: Datacolor Holding AG, Lucerne (CH)

( * ) Notice: Subject to any disclaimer, the term of this patent is extended or adjusted under 35 U.S.C. 154(b) by 231 days.

(21) Appl. No.: 14/453,424

(22) Filed: Aug. 6, 2014

(65) Prior Publication Data

US 2015/0198522 A1 Jul. 16, 2015

Related U.S. Application Data

(60) Provisional application No. 61/927,812, filed on Jan. 15, 2014.

(51) Int. Cl.
| | | |
|---|---|---|
| *G01J 3/52* | (2006.01) | |
| *G01N 21/25* | (2006.01) | |
| *G01J 3/46* | (2006.01) | |
| *G01J 3/50* | (2006.01) | |
| *G01N 21/57* | (2006.01) | |

(52) U.S. Cl.
CPC ............... *G01N 21/251* (2013.01); *G01J 3/463* (2013.01); *G01J 3/501* (2013.01); *G01N 21/57* (2013.01); *G01N 2201/0221* (2013.01); *G01N 2201/065* (2013.01); *G01N 2201/0627* (2013.01)

(58) Field of Classification Search
CPC ............... G01J 3/46; G01J 3/50; G01N 21/25
USPC ................................... 356/402–425
See application file for complete search history.

(56) References Cited

U.S. PATENT DOCUMENTS

| | | | |
|---|---|---|---|
| 7,057,641 B2 | 6/2006 | Bodnar et al. | |
| 7,554,586 B1 | 6/2009 | Imai et al. | |
| 9,204,115 B1 | 12/2015 | Yu | |
| 2011/0176029 A1* | 7/2011 | Boydston | H04N 1/46 348/223.1 |

OTHER PUBLICATIONS

Color-Helper Professional Quick Reference Guide, 2008, downloaded from color-helper.com, pp. 1-7.

\* cited by examiner

*Primary Examiner* — Abdullahi Nur

(57) ABSTRACT

An apparatus for assisting in measuring a color of a target includes an enclosed housing having a first aperture formed in a first end and a second aperture formed in an opposite second end and aligned concentrically with the first aperture, an array of light emitting diodes positioned inside the housing, between the first aperture and the second aperture, and an array of reference colors having known reflectance spectra, the array of reference colors being removably positioned inside the housing, between the array of light emitting diodes and the second aperture.

24 Claims, 11 Drawing Sheets

400

800

METHOD AND APPARATUS FOR IMAGE-BASED COLOR MEASUREMENT USING A SMART PHONE

CROSS REFERENCE TO RELATED APPLICATIONS

This application claims the benefit of U.S. Provisional Patent Application Ser. No. 61/927,812, filed Jan. 15, 2014, which is herein incorporated by reference in its entirety.

FIELD OF THE INVENTION

The present invention generally relates to the field of imaging, and more specifically relates to color measurement.

BACKGROUND

Color measurement systems help to improve operational efficiency and product quality in supply chains. For example, color approval offices for the global apparel supply chain, apparel mills and dye houses, paint stores, textile printing shops, carpet manufacturers, manufacturers of wood panels, tiles, vinyl sheets, and laminates, and other industries relying on the digital color workflow require accurate color evaluation and visualization.

However, color measurement is often desirable in less formal circumstances as well. For instance, one might wish to measure the color of the paint on a wall and find a closest matching color from a database of stored colors. In such cases, the equipment available to perform color measurement is usually less sophisticated than that used in industrial supply chains. For instance, the average person does not typically keep dedicated color measurement equipment, such as a spectrophotometer, on hand.

SUMMARY OF THE INVENTION

An apparatus for assisting in measuring a color of a target includes an enclosed housing having a first aperture formed in a first end and a second aperture formed in an opposite second end and aligned concentrically with the first aperture, an array of light emitting diodes positioned inside the housing, between the first aperture and the second aperture, and an array of reference colors having known reflectance spectra, the array of reference colors being removably positioned inside the housing, between the array of light emitting diodes and the second aperture.

A system for measuring a color of a target includes an image capturing device for capturing an image of the target, an apparatus detachably coupled to the image capturing device, the apparatus including an enclosed housing having a first aperture formed in a first end and a second aperture formed in an opposite second end, wherein a lens of the image capturing device is aligned concentrically with the first aperture and the second aperture, such that the second aperture is positioned approximately at a center of a field of view of the image capturing device, an array of light emitting diodes positioned inside the housing, between the first aperture and the second aperture, and an array of reference colors having known reflectance spectra, the array of reference colors being removably positioned inside the housing, between the array of light emitting diodes and the second aperture, and a processor for processing the image of the target to estimate the color.

An apparatus for assisting in measuring a color of a target includes an integrating sphere, a sample port formed in the integrating sphere, an imaging port formed in the integrating sphere, on an opposite side of the integrating sphere from the sample port, a light source port formed in the integrating sphere, near the imaging port, for coupling light emitted from outside of the integrating sphere into the integrating sphere, and an array of reference colors having known reflectance spectra, the array of reference colors being arranged on a ring that is positioned at the sample port.

A method for measuring a color of a target includes capturing a plurality of images, each of the plurality of images depicting a plurality of reference colors and at least a portion of the target, wherein reflectance spectra of the plurality of reference colors is known, wherein each of the plurality of images is captured under a known illuminant, estimating an average reflectance of the target in accordance with the plurality of images, and calculating color tristimulus values of the target in accordance with the average reflectance, the known illuminant, and color matching functions, wherein the capturing, the estimating, and the calculating are all performed by a computing device including an integrated color camera.

A computer readable storage device contains an executable program for measuring a color of a target, where the program performs steps including capturing a plurality of images, each of the plurality of images depicting a plurality of reference colors and at least a portion of the target, wherein reflectance spectra of the plurality of reference colors is known, wherein each of the plurality of images is captured under a known illuminant, estimating an average reflectance of the target in accordance with the plurality of images, and calculating color tristimulus values of the target in accordance with the average reflectance, the known illuminant, and color matching functions, wherein the computer readable storage device is part of a computing device including an integrated color camera.

BRIEF DESCRIPTION OF THE DRAWINGS

The teachings of the present invention can be readily understood by considering the following detailed description in conjunction with the accompanying drawings, in which.

DETAILED DESCRIPTION

In one embodiment, the present invention is a method and apparatus for image-based color measurement using a smart phone. Embodiments of the invention provide a small (e.g., handheld) device that can be attached to a mobile phone having an integrated color camera (e.g., a smart phone) and used to measure the color of a target. For instance, this might allow the mobile phone to be used to capture an image of the paint on a wall and produce the closest palette color from a database of stored colors. In-situ calibration using a plurality of reference colors from the same image of the target under one or more known illuminants ensures highly accurate and repeatable color measurement.

Figure 1:
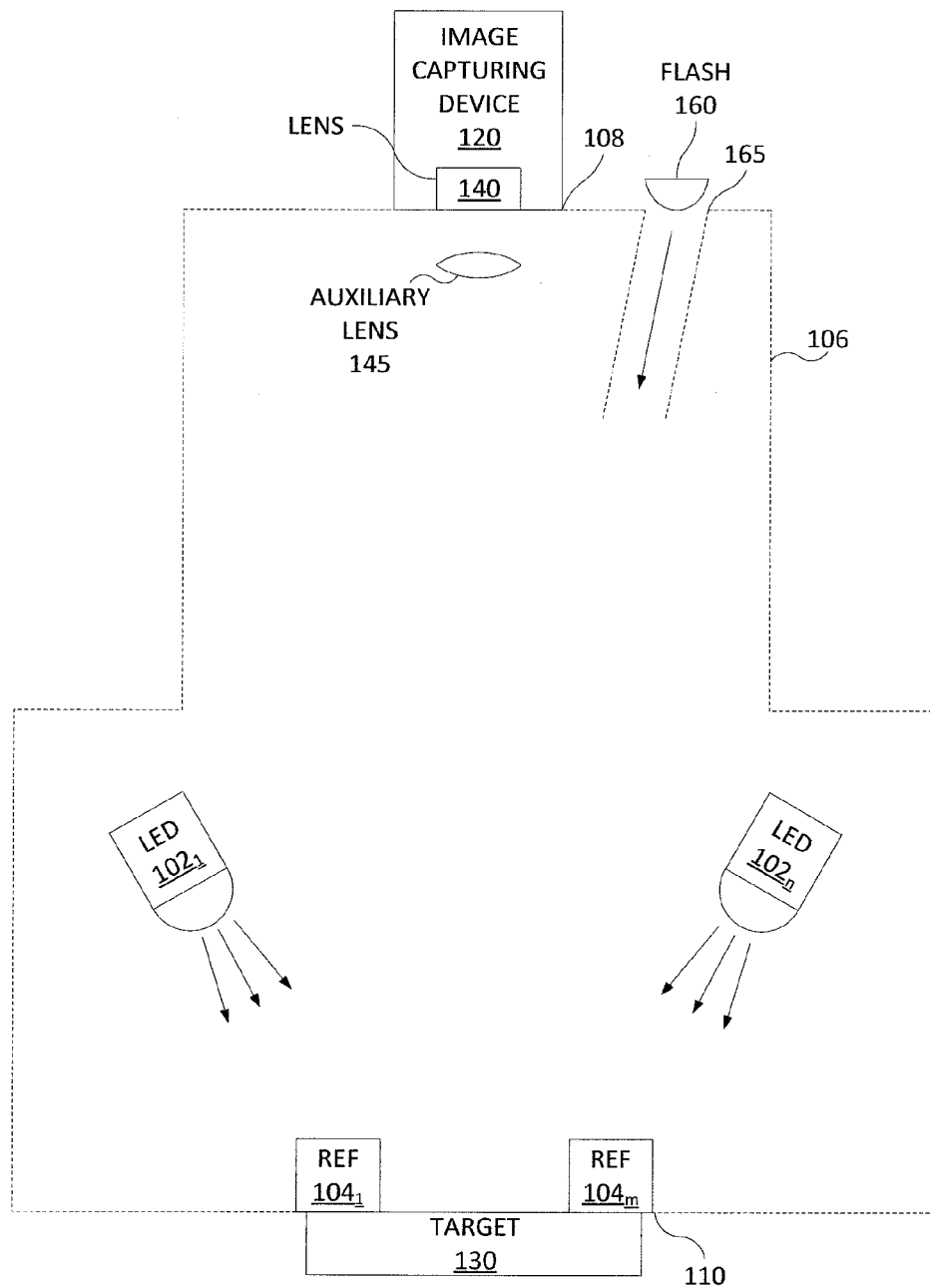
FIG. 1 is a block diagram illustrating one embodiment of a system for image-based color measurement, according to the present invention.

FIG. 1 is a block diagram illustrating one embodiment of a system 100 for image-based color measurement, according to the present invention. The system 100 is designed to be attached to an image capturing device 120, such as a smart phone with an integrated color camera. The image capturing device 120 executes a software application (alone, or in conjunction with a wirelessly connected computing device) that guides a user through the color measurement process using the system 100. The software application may control both the image capturing device 120 and components of the system 100 (e.g., illuminant sources). The software application may further perform image processing, color calibration, color tristimulus value estimation, color identification, and glossiness estimation, as discussed in further detail below.

As illustrated, the system 100 generally comprises an array of light emitting diodes $102_1$-$102_n$ (hereinafter collectively referred to as "LEDs 102") and an array of reference colors $104_1$-$104_m$ (hereinafter collectively referred to as "reference colors 104"). The LEDs 102 and reference colors 104 are contained within a housing 106.

The housing 106 includes a first aperture 108 and a second aperture 110. The first aperture 108 comprises a camera aperture that is configured for alignment with the image capturing device 120, and more particularly with the lens 140 of the image capturing device 120. The first aperture 108 may be generally circular in shape (i.e., having the approximate shape of a circle, if not perfectly circular). In one embodiment, the system 100 optionally includes a long tube 165 for aligning with a flash 160 of the image capturing device 120 for gloss measurements. In one embodiment, the system 100 further includes an optional auxiliary lens 145, described in greater detail below. The second aperture 110 comprises a target aperture that is configured for alignment with the target 130 whose color is to be measured, and may also be generally circular in shape.

The array of LEDs 102 comprises a plurality of LEDs 102 of different spectral types. In one embodiment, the LEDs 102 are arranged in a ring around a printed circuit board strip. In a further embodiment still, each of the LEDs 102 is positioned to illuminate the target 130 and reference colors 104 at an angle of approximately forty-five degrees. One or more of the LEDs 102 may be covered by a narrow-band interference or non-interference filter.

In one embodiment, the array includes twenty-seven LEDs 102. In a further embodiment, at least three LEDs of each of nine different spectral types are positioned around the ring in intervals of approximately 120 degrees for illumination homogeneity. The nine different spectral types include narrow-band spectra with peak wavelengths covering the visual range from approximately four hundred to approximately seven hundred nanometers. For instance, the spectral types may include the following exemplary set of nine peak wavelengths: 405 nm, 425 nm, 465 nm, 520 nm, 560 nm, 580 nm, 645 nm, 666 nm, or 700 nm. In a further embodiment, these spectral types can be grouped into three sets: (1) a first group containing the peak wavelengths of 405 nm, 52 nm, and 645 nm; (2) a second group containing the peak wavelengths of 425 nm, 560 nm, and 666 nm; and (3) a third group containing the peak wavelengths of 465 nm, 580 nm, and 700 nm.

In another embodiment, the array includes twenty-one LEDs 102. In a further embodiment, at least three LEDs of each of seven different spectral types are positioned around the ring in intervals of approximately 120 degrees for illumination homogeneity. The seven different spectral types include a broad-band white spectrum and six narrow-band spectra with peak wavelengths covering the visual range from approximately four hundred to approximately seven hundred nanometers. For instance, the spectral types may include the following exemplary set of six narrow-band peak wavelengths: 400 nm, 460 nm, 520 nm, 580 nm, 640 nm, and 700 nm. In a further embodiment, the seven spectral types can be grouped into three sets: (1) a first group containing only the broad-band white spectrum; (2) a second group containing the peak wavelengths of 400 nm, 520 nm, and 580 nm; and (3) a third group containing the peak wavelengths of 460 nm, 580 nm, and 700 nm.

Figure 4:
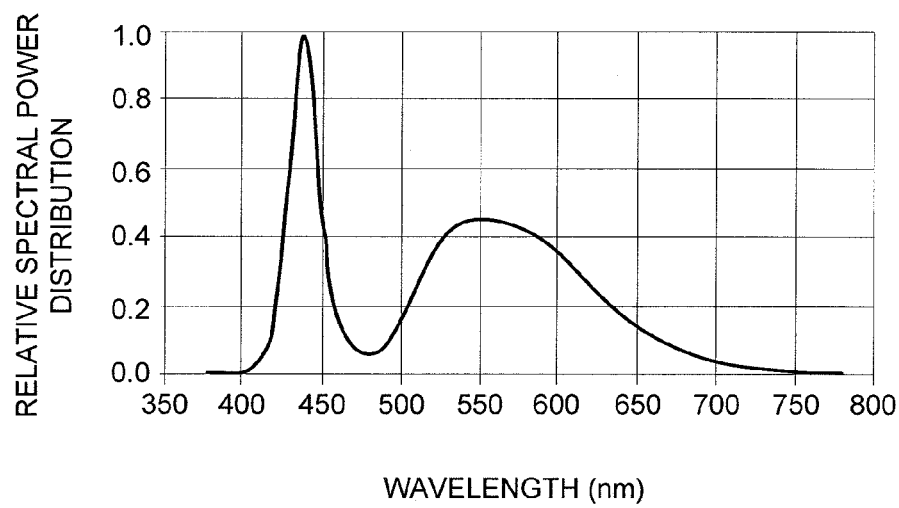
FIG. 4 is a chart illustrating the spectral power distribution of a cool-white LED.

In another embodiment still, the array includes twenty-seven LEDs 102, including the same white spectrum illustrated in the chart 400 of FIG. 4. In particular, chart 400 illustrates the spectral power distribution of a cool-white LED. At least three LEDs of each of nine different spectral types are positioned around the ring in intervals of approximately 120 degrees for illumination homogeneity. In addition, the array includes nine different types of narrow-band interference filters with peak wavelengths covering the visible range, where each filter covers three LEDs that are separated by 120 degrees.

The array of reference colors 104 comprises a plurality of swatches of different colors. In one embodiment, the array includes thirty-six reference colors 104, the reflectance spectra of which are characterized prior to measuring the target 130 and stored in memory (e.g., local memory of the image capturing device 120 or remote memory of a wirelessly coupled computing device). In one embodiment, the reference colors 104 are arranged in a ring that is positioned around the second aperture 110 and is almost flush with the plane of the target 130. In a further embodiment, the array of reference colors 104 is detachable from the housing 106 (e.g., using adhesive or other mechanical mechanism).

In one embodiment, the system 100 further includes a cap (not shown) that fits over the second aperture 110. The cap has an interior surface that faces the inside of the housing 106 and is uniformly coated with a neutral matte gray color for illumination uniformity correction, as discussed in greater detail below.

Figure 2:
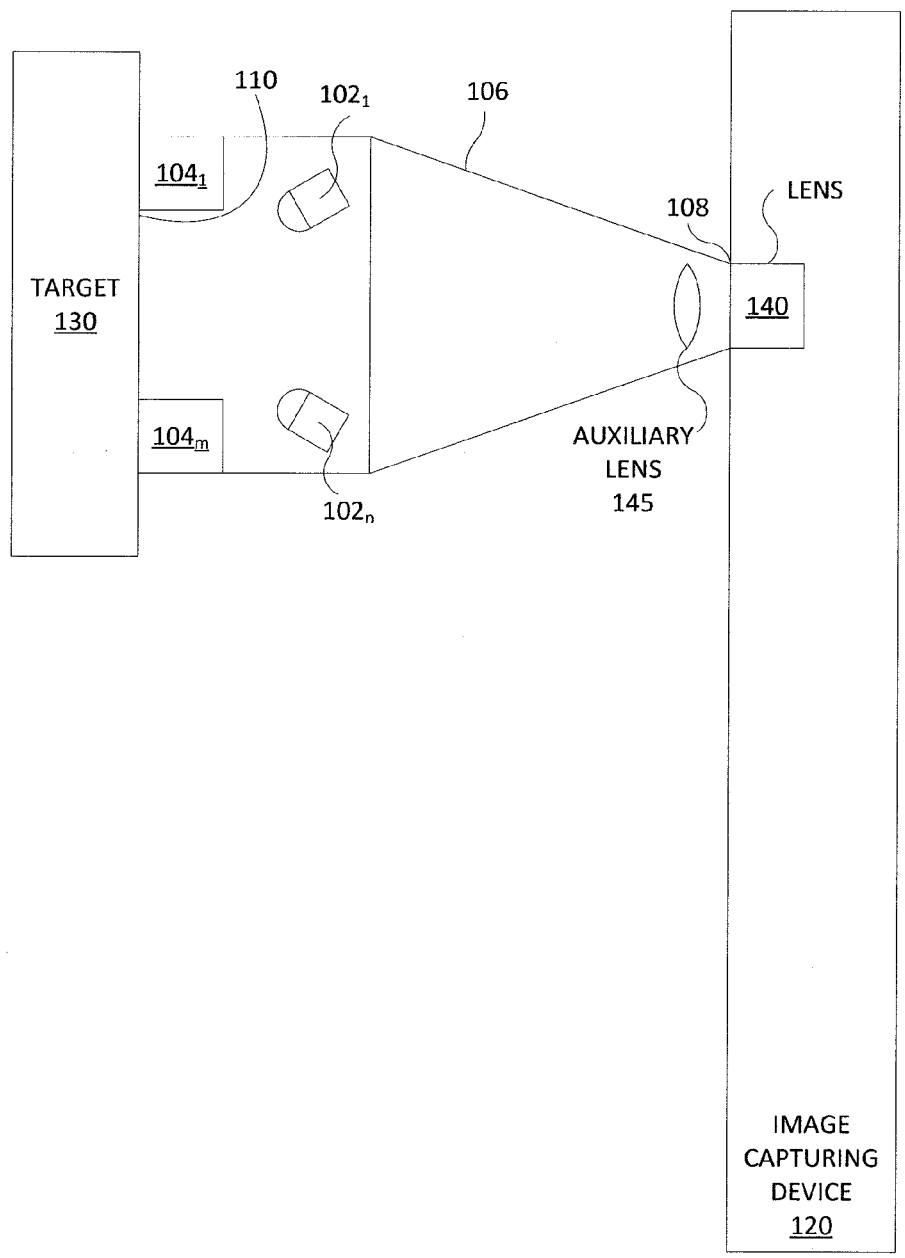
FIG. 2 is a schematic diagram illustrating the system of FIG. 1 in use, according to embodiments of the present invention.

FIG. 2 is a schematic diagram illustrating the system 100 of FIG. 1 in use, according to embodiments of the present invention. As illustrated, the first aperture 108, the second aperture 110, the lens 140 of the image capturing device 120 (e.g., a smart phone with an integrated color camera), and optionally the auxiliary lens 145, are aligned concentrically, so that the second aperture 110 is positioned approximately at the center of the image capturing device's field of view, and the image capturing device 120 receives the light reflecting from the target 130 at an approximately zero-degree angle. In one embodiment, the optional auxiliary lens 145 comprises a strong lens with a short focal length, e.g., at most 3 centimeters. For example, a typical value of the focal length may comprise approximately 24 mm. Notably, in many cases, lenses integrated within smartphones or other devices are not capable of focusing at very close objects. Thus, the use of an auxiliary lens 145 allows the housing to be sized to just slightly longer than the focal length of the auxiliary lens 145 (e.g., a distance from the first aperture 180 to the second aperture 110). This allows the system 100 to have a size that works well with, and is complementary to the size of current handheld devices. In general, the focal length is such that the entire sample area including reference colors is fit into the image, and such that the field of view is at least more than half covered by the sample area.

Figure 3:
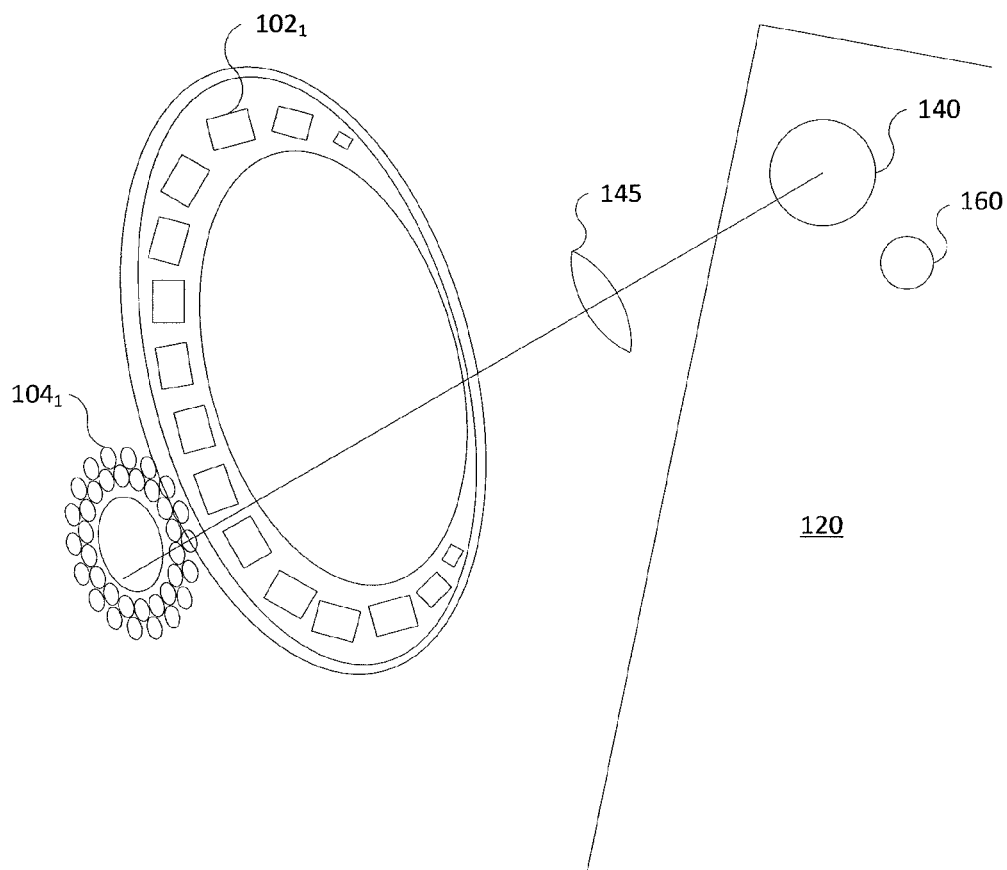
FIG. 3 is a schematic diagram illustrating the system of FIG. 1 in use, but with the housing removed to better illustrate the orientation of components.

FIG. 3 is a schematic diagram illustrating the system 100 of FIG. 1 in use, but with the housing 106 removed to better illustrate the orientation of components. As discussed above, the second aperture 110 of the system 100 is positioned at the center of the image capturing device's field of view and is surrounded by the reference colors 104.

If the lens 140 and flash 160 of the image capturing device 120 are close enough to each other, then they can work together as a gloss meter to measure the glossiness of the target 130. In this case, the light emitted by the flash 160 is collimated through the long tube 165 and illuminates the target 130 at an angle of approximately eight degrees.

Figure 5:
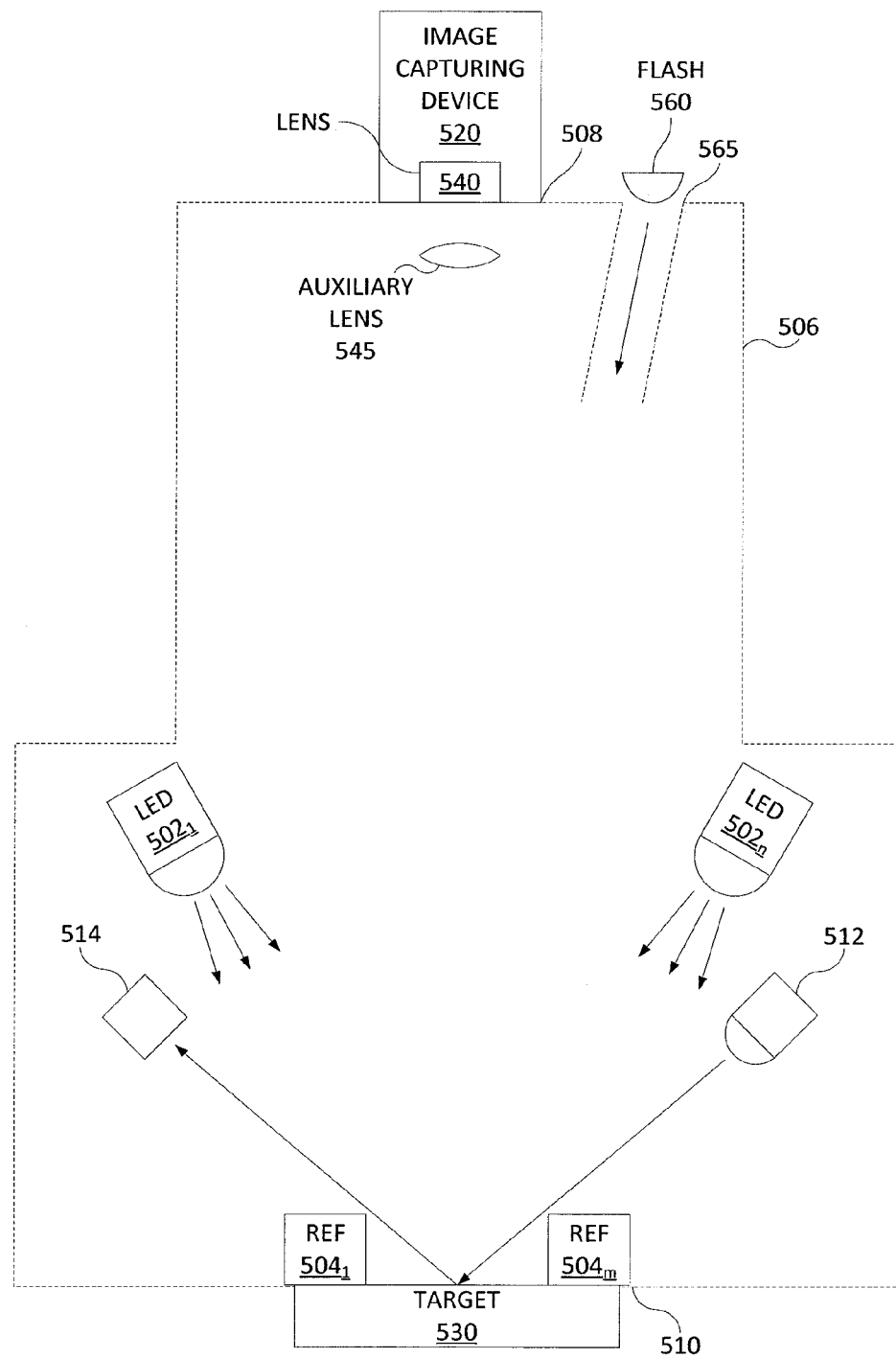
FIG. 5 is a block diagram illustrating a second embodiment of a system for image-based color measurement, according to the present invention.

FIG. 5 is a block diagram illustrating a second embodiment of a system 500 for image-based color measurement, according to the present invention. The system 500 is substantially similar to the system 100 illustrated in FIG. 1. For instance, the system 500 generally comprises an array of light emitting diodes $502_1$-$502_n$ (hereinafter collectively referred to as "LEDs 502") and an array of reference colors $504_1$-$504_n$ (hereinafter collectively referred to as "reference colors 504"). The LEDs 502 and reference colors 504 are contained within a housing 506.

The housing 506 includes a first aperture 508 and a second aperture 510. The first aperture 508 comprises a camera aperture that is configured for alignment with the image capturing device 520, and more particularly with the lens 540 of the image capturing device 520. The system 500 may optionally include an auxiliary lens 545 having a similar purpose and function as that of auxiliary lens 145 in FIGS. 1-3. The first aperture 508 may be generally circular in shape (i.e., having the approximate shape of a circle, if not perfectly circular). The second aperture 510 comprises a target aperture that is configured for alignment with the target 530 whose color is to be measured, and may also be generally circular in shape.

In addition, the system 500 further includes a single LED 512 (or other type of small form factor light source) cooperating with a photodiode/pixel detector 514. The single LED 512 and the pixel detector 514 are positioned on opposite sides of the second aperture 510 and are used to measure the glossiness of the target 530. According to American Society for Testing and Materials (ASTM) standards for a medium-gloss target, in one embodiment both the single LED 512 and the pixel detector 514 are positioned at reception angles of approximately sixty degrees. The system 500 may optionally include a long tube 565 for aligning with a flash 560 of the image capturing device 520 for gloss measurements. For instance, the long tube 565 may have the same orientation and function as long tube 165 in the preceding figures. Notably, while inclusion of these components is not necessary in view of the inclusion of the LED 512 and pixel detector 514, in one embodiment, both techniques for measuring gloss may be utilized on conjunction with one another.

Figure 6:
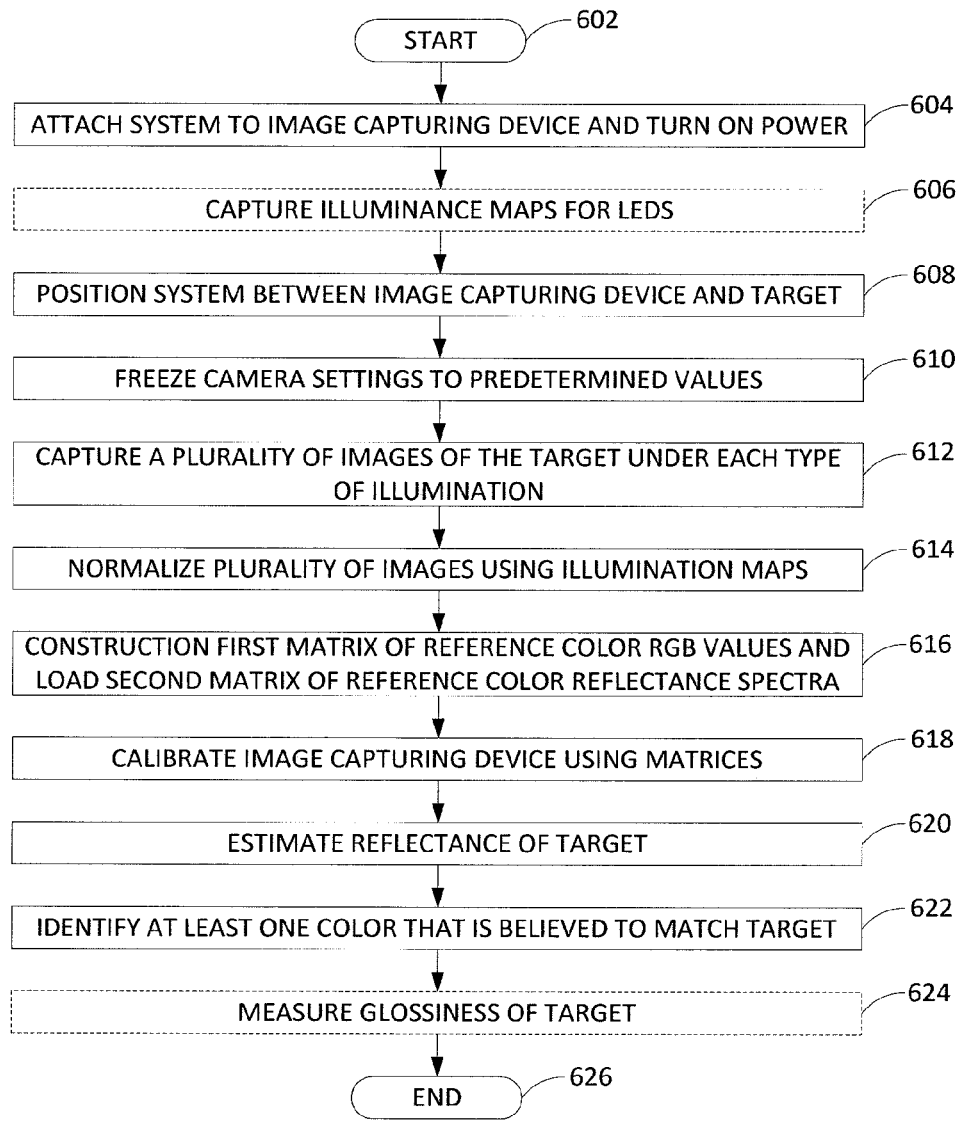
FIG. 6 is a flow diagram illustrating one embodiment of a method for measuring the color of a target, according to the present invention.

FIG. 6 is a flow diagram illustrating one embodiment of a method 600 for measuring the color of a target, according to the present invention. The method 600 may be implemented by the system 100 or the system 500 illustrated in the previous Figures, operating in conjunction with a software application that executes at the image capturing device and/or a wirelessly coupled remote computing device. As such, reference is made in the discussion of the method 600 to various components of the system 100. It will be appreciated, however, that operation of the method 600 is not limited to the configuration of the system 100.

The method 600 starts in step 602.

In step 604, the system 100 is attached to the image capturing device (e.g., a smart phone having an integrated color camera) through an adapter, and the system power is turned on.

In optional step 606 (illustrated in phantom), illuminance maps ($W_1$~$W_m$) for the LEDs are camera-captured. In one embodiment, the illuminance maps are captured for each spectral type ($S_1$~$S_m$) of LED, each group ($G_1$~$G_m$) of spectral types, or under each type of interference filter ($F_1$~$F_m$). Capturing the illuminance maps involves turning each of the LEDs of each spectral type, group, or interference filter while the cap covers the second aperture 110 (i.e., the reference colors 104 are removed from the system 100) and capturing an image. In one embodiment, for each illumination geometry, an illumination uniformity correction is performed by dividing each test image, pixel-by-pixel, by the illuminance map W (i.e., the image of the cap) and then multiplying the dividend by the reflectance of the gray. If the illuminance maps were captured within a threshold period of time (e.g., a few hours or days), step 606 can be skipped.

In step 608, the system 100 is positioned between the image capturing device 120 and the target 130. For instance, the system 100 is assembled and positioned relatively to the image capturing device 120 and the target 130 as illustrated in FIG. 2. At this point, the cap is removed from the second aperture 110, and the reference colors 104 are positioned as illustrated in FIG. 1.

In step 610, the image capturing device 120 (or a remote computer communicating wirelessly with the image capturing device 120) freezes all of the camera settings of the image capturing device 120 to predetermined values. The frozen settings include, for example, exposure time and white balance.

In step 612, the image capturing device 120 captures a plurality of images of the target 130 under each type of illumination (e.g., under the LEDS of each spectral type, in each group, or under each type of interference filter).

In step 614, the image capturing device 120 (or a remote computer communicating wirelessly with the image capturing device 120) normalizes each of the plurality of images with the corresponding illumination maps ($W_1$~$W_m$).

In step 616, the image capturing device 120 (or a remote computer communicating wirelessly with the image capturing device 120) constructs first and second matrices. The first matrix is a 3m×K matrix (referred to as "D"), where m is the number of the plurality of images and K is the number of reference colors 104. The first matrix D contains the red, green, and blue (RGB) values of the reference colors 104 under the illuminants, as extracted from each of the plurality of images. The second matrix is a P×K matrix (referred to as $R_T$), where P is the number of data points in each spectrum. The second matrix $R_T$ contains the reflectance spectra of the reference colors 104.

In step 618, the image capturing device 120 is calibrated using the matrices. In one embodiment, calibration is performed by first estimating a third, P×3m matrix (referred to as "M") and an offset P-vector (b) that map (as closely as possible) the camera RGB matrix (referred to as "D") to the corresponding reflectance matrix $R_T$. This mapping may be expressed as:

$$R_T = MD + b \quad \text{(EQN. 1)}$$

EQN. 1 may be further expressed as a homogeneous equation:

$$R_T = M_A D_A \quad \text{(EQN. 2)}$$

where $M_A = [M\ b]$ is the P×(3m+1) matrix comprising M right-augmented by the column vector b, and $D_A = [D'\ 1']'$ is the (3m+1)×K matrix comprising D augmented from the bottom by a row K-vector 1 of ones. Here, D' is the transpose of D. To estimate $M_A$, a least square approximation may be used, such as:

$$M_A = R_T \text{pinv}(D_A) = R_T D_A'(D_A D_A')^{-1} \quad \text{(EQN. 3)}$$

In step 620, the image capturing device 120 (or a remote computer communicating wirelessly with the image capturing device 120) estimates the reflectance of the target 130. In one embodiment, an estimated reflectance P-vector (referred to as "r") can be computed for each pixel of the target 130 from its measured camera 3m+1 vector $d_A$ (i.e., the column vector d extended by a one at the end) as such:

$$R_a = M_A d_A \quad \text{(EQN. 4)}$$

The average reflectance ($\overline{d_A}$) of the target 130 can be further estimated by averaging the reflectances ($d_A$) of all of the pixels that belong to the target 130. Within the context of the present invention, "average reflectance" refers to spatial average over the displayed part of the target 130. Then, the color tristimulus values of the target 130 can be further calculated from the average reflectance, the predefined illuminant, and Commission Internationale de l'Eclairage (CIE) color matching functions.

In step 622, the image capturing device 120 (or a remote computer communicating wirelessly with the image capturing device 120) identifies at least one stored color that is believed to match the color of the target 130. In one embodiment, the image capturing device 120 searches a color database containing a large pool of standard colors and suggests at least a predefined number (e.g., three) of those colors that exhibit a smallest color difference relative to the estimated tristimulus values of the target 130. The identified colors may be displayed to a user (e.g., on a screen of the image capturing device 120) and/or stored for future reference.

In optional step 624 (illustrated in phantom), the image capturing device 120 (or a remote computer communicating wirelessly with the image capturing device 120) measures the glossiness of the target 130. Estimating the glossiness will further refine the selection of a matching color. In one embodiment, the glossiness is estimated as "matte," "semi-gloss," or "glossy." The glossiness may be measured using a built-in flash in the image capturing device 120 (e.g., as illustrated in FIG. 1) or using an LED and photodiode pair (e.g., as illustrated in FIG. 5). A more quantitative assessment of glossiness can be made by pre-calibrating the gloss assessment against samples whose glossiness is known.

The method 600 ends in step 626.

Thus, the system 100 (or 300) captures a plurality of images containing both the target 130 and the reference colors 104 under sequential illumination by the LEDs 102 having the same spectral types (or the groups of LEDs 102 having different spectral types). From the captured images and the known reflectance spectra of the reference colors 104, the color of the target 130 can be accurately estimated. In addition to the color, the system 100 can also measure the glossiness of the target 130 using the flash of the image capturing device 120.

Figure 7:
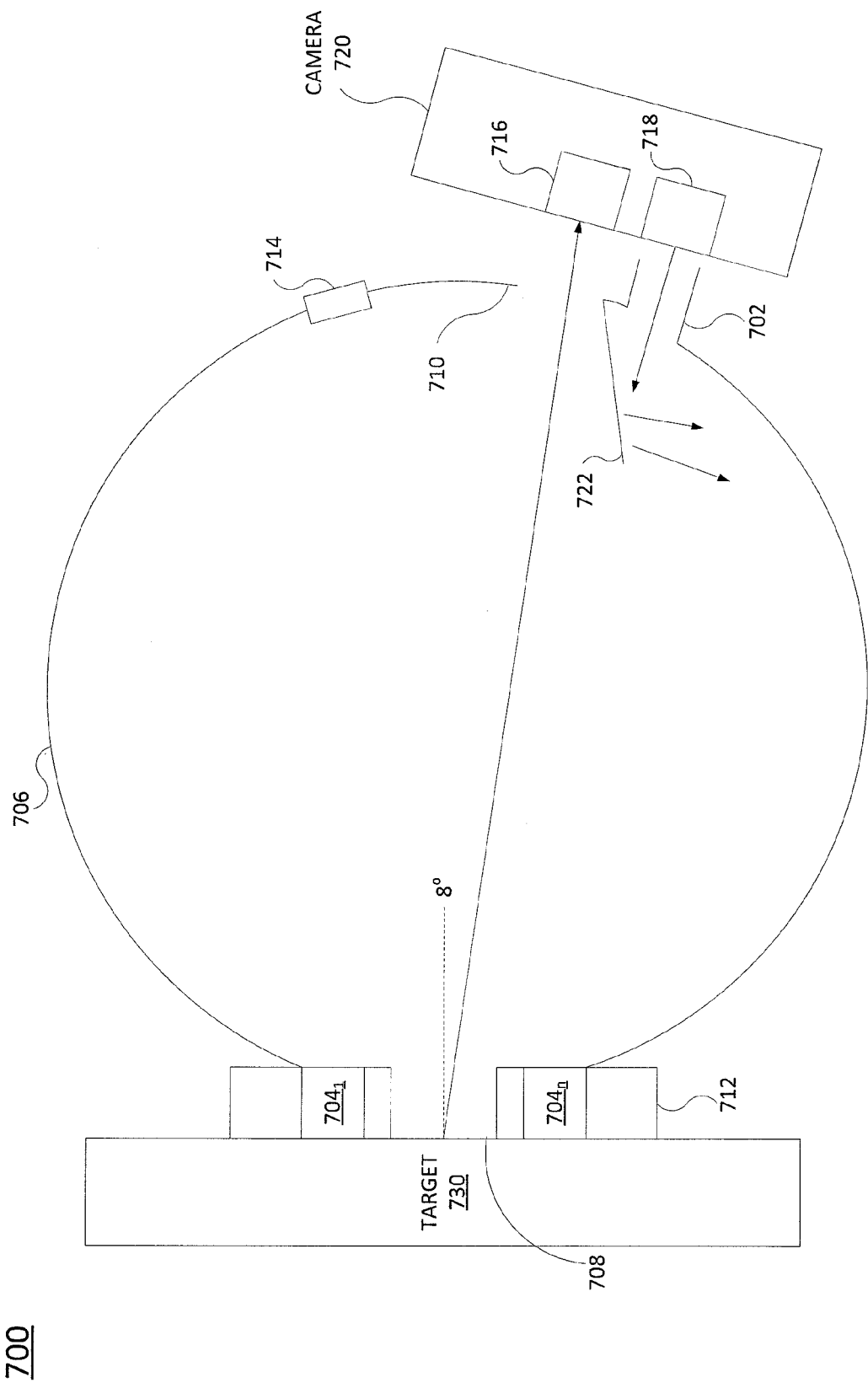
FIG. 7 is a block diagram illustrating a third embodiment of a system for image-based color measurement, according to the present invention.

FIG. 7 is a block diagram illustrating a third embodiment of embodiment of a system 700 for image-based color measurement, according to the present invention. The system 700 is designed to be attached to an image capturing device 720, such as a smart phone with an integrated color camera. The image capturing device 720 executes a software application (alone, or in conjunction with a wirelessly connected computing device) that guides a user through the color measurement process using the system 700.

As illustrated, the system 700 generally comprises an integrating sphere 706. The integrating sphere 706 further includes a light source port 702, an array of reference colors $704_1$-$704_n$ (hereinafter collectively referred to as "reference colors 704"), a sample port 708, an imaging port 710, and a detachable gloss trap 714.

The light source port 702 includes a light pipe that couples light from the flash 718 of the image capturing device 720 into the integrating sphere 706. The coupled light is at least partially deflected by baffle 722 and scattered by the integrating sphere 706 and eventually illuminates the sample port 708 uniformly at hemisphere angles. In various examples, an orientation angle of the baffle 722 (e.g., with respect to a line perpendicular to a tangent line of the integrating sphere 706) may comprise substantially any angle so long as light from the flash 718 does not directly illuminate any portion of the reference colors 704 or the target 730. In other words, light from the flash 718 should reflect off at least one portion of the inner surface of integrating sphere 706 before reaching the reference colors 704 and target 730.

In one embodiment, the reference colors 704 are mounted on a thin plate 712 that is positioned at the sample port 708. The center of the plate 712 is open to the target 730 whose color is being measured.

Figure 8:
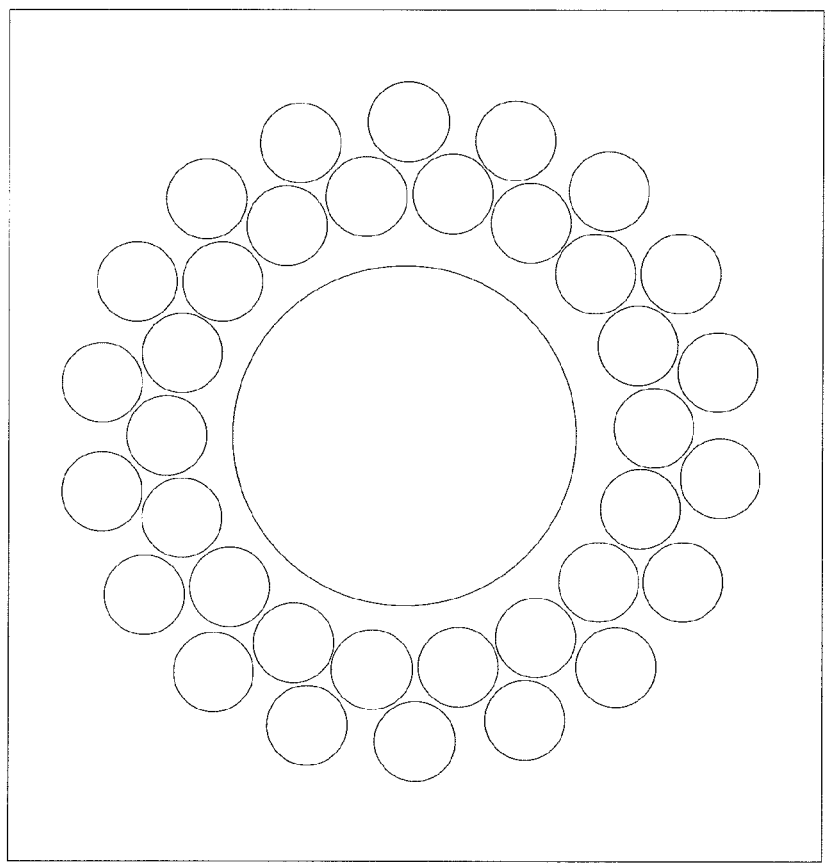
FIG. 8 is a simulation of an image that the image capturing device of FIG. 7 will capture.

The imaging port 710 allows the lens 716 of the image capturing device 720 to capture an image containing the target 730 and all of the reference colors 704. In one embodiment, the viewing angle of the image capturing device 720 is offset by approximately eight degrees to prevent inter-reflection between the target 730 and the image capturing device 720 (as recommended by the CIE). FIG. 8 is a simulation 800 of an image that the image capturing device 720 of FIG. 7 will capture.

The gloss trap 714 is positioned on an opposite side of the integrating sphere 706 from the sample port 708 and is detachable. In one embodiment, the gloss trap 714 is positioned approximately eight degrees on one side of the target normal, whereas the image center of the image capturing device 720 is approximately eight degrees to the other side of the normal; this creates a specular path from the gloss trap 714 to the target 730 to the image capturing device 720. The specular excluded (SPEX) and the specular included (SPIN) measurements are performed with and without the gloss trap 714 for gloss estimation.

In one embodiment, the system 700 further includes a cap (not shown) that fits over the sample port 708. The cap has an interior surface that faces the inside of the integrating sphere 706 and is uniformly coated with a neutral matte gray color for illumination uniformity correction, as discussed in greater detail below.

Figure 11:
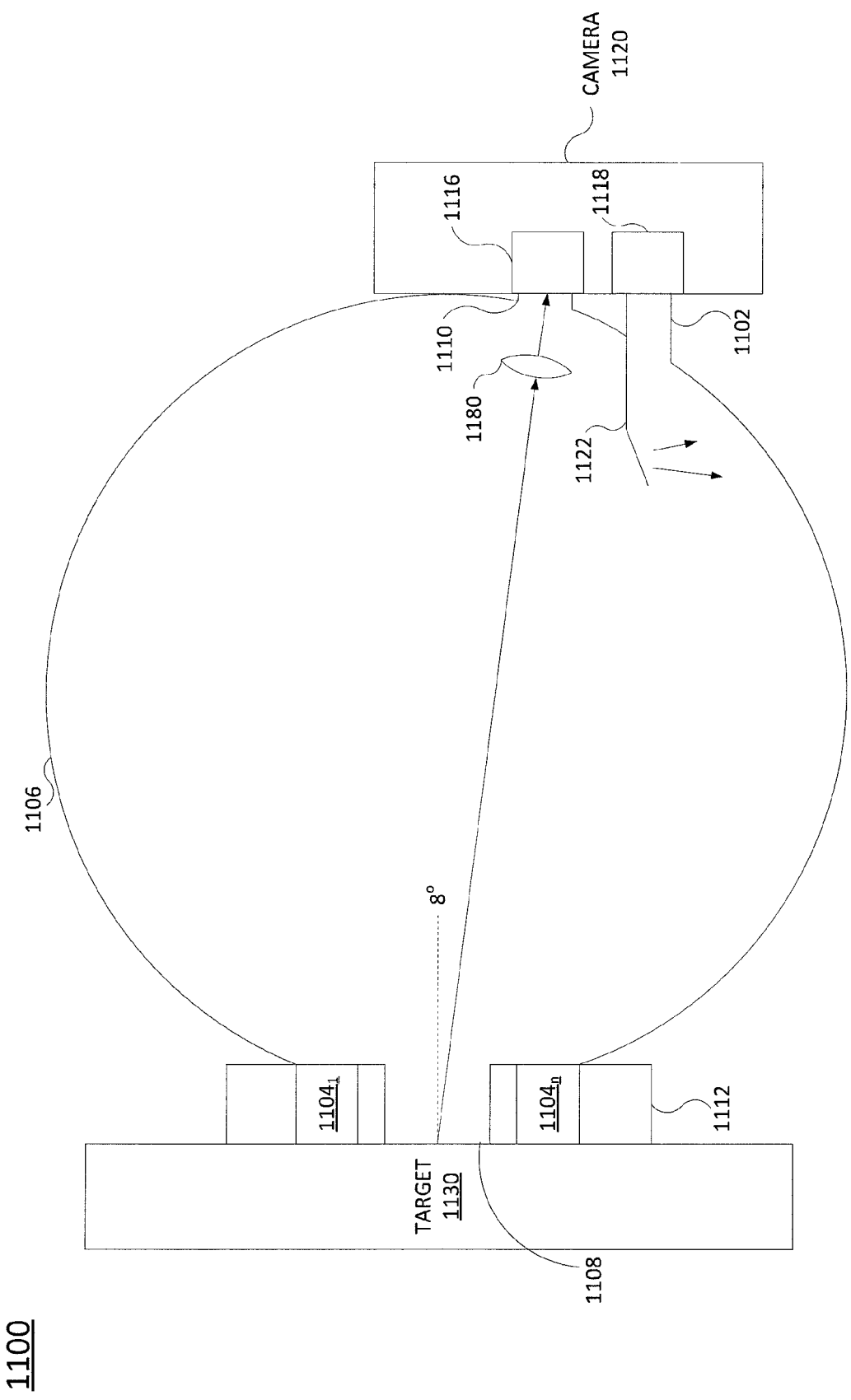
FIG. 11 is a block diagram illustrating a fourth embodiment of a system for image-based color measurement, according to the present invention.

FIG. 11 is a block diagram illustrating a fourth embodiment of embodiment of a system 1100 for image-based color measurement, according to the present invention. The system 1100 is substantially similar to the system 700 illustrated in FIG. 7. For example, system 1100 generally comprises an integrating sphere 1106 that includes a light source port 1102, an array of reference colors 1104₁-1104ₙ (hereinafter collectively referred to as "reference colors 704"), a sample port 1108, an imaging port 1110. However, system 1100 further includes an auxiliary lens 1180, or "imaging lens" added between the target 1130 and the camera 1120. A typical camera cannot focus on a sample that is very close to the camera. Thus, the additional lens 1180 allows the camera 1120 to capture a clear image of the target 1130 when the target 1130 is very close to the camera 1120, e.g., at a distance of at most approximately 3 centimeters. In general, the focal length is such that the entire sample area including reference colors is fit into the image, and such that the field of view is at least more than half covered by the sample area.

Similar to the example of FIG. 7, the light source port 1102 of system 1100 includes a light pipe that couples light from the flash 1118 of the image capturing device 1120 into the integrating sphere 1106. In various examples, an orientation angle of the baffle 1122 (e.g., with respect to a line perpendicular to a tangent line of the integrating sphere 1106) may comprise substantially any angle so long as light from the flash 1118 does not directly illuminate any portion of the reference colors 1104 or the target 1130. Thus, in such embodiments, coupled light is at least partially deflected by baffle 1122 and scattered by the integrating sphere 1106 and eventually illuminates the sample port 1108 uniformly at hemisphere angles. However, in one particular embodiment, the baffle 1122 is oriented perpendicular to the sample/target 1130, as described in greater detail below.

In one embodiment, the reference colors 1104 are mounted on a thin plate 1112 that is positioned at the sample port 1108. The center of the plate 1112 is open to the target 1130 whose color is being measured.

The imaging port 1110 allows the lens 1116 of the image capturing device 1120 to capture an image containing the target 1130 and all of the reference colors 1104. In one embodiment, the viewing angle of the image capturing device 1120 is offset by approximately eight degrees to prevent inter-reflection between the target 1130 and the image capturing device 1120.

In one particular embodiment, the principal ray of lens 1116 and the flash 1118 are substantially parallel to each other and/or substantially perpendicular to the target 1130. The orientation angle of baffle 1122 may also be substantially parallel to the principal ray of lens 1116 and the flash 1118, so long as the criteria is satisfied that light from the flash 1118 does not directly illuminate any portion of the reference colors 1104 or the target 1130. In addition, in one embodiment the position, tilting axis, and the focal length of the auxiliary lens 1180 can be arranged to allow the camera 1120 to capture the entire area of the target 1130 and all of the reference colors 1104.

Notably, the system 1100 is capable of capturing an image in a similar manner to that of system 700 of FIG. 7. Thus, FIG. 8 may also represent a simulation of an image that the image capturing device 1120 of FIG. 11 will capture. In one embodiment, the system 1100 may further include a cap (not shown) that fits over the sample port 1108. The cap has an interior surface that faces the inside of the integrating sphere 1106 and is uniformly coated with a neutral matte gray color for illumination uniformity correction, as discussed in greater detail below.

Figure 9:
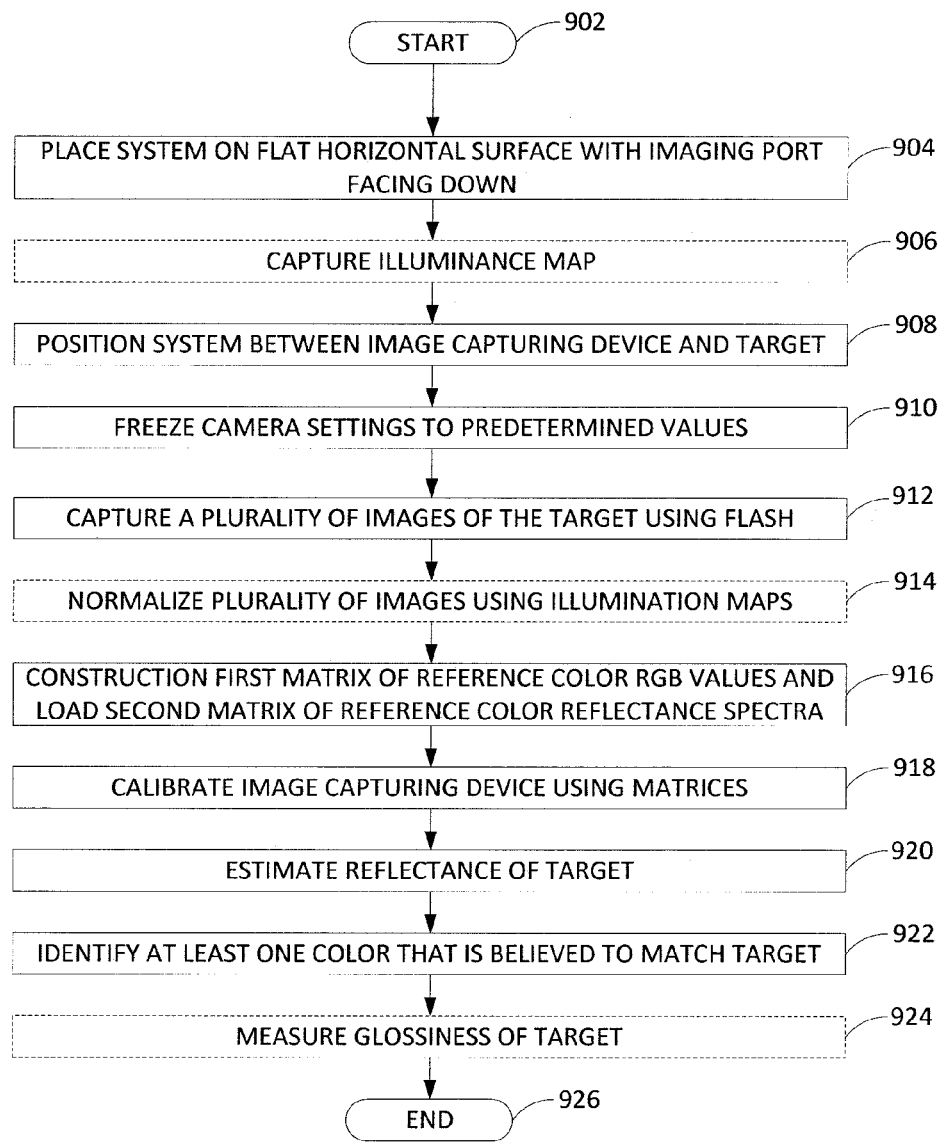
FIG. 9 is a flow diagram illustrating one embodiment of a method for measuring the color of a target, according to the present invention.

FIG. 9 is a flow diagram illustrating one embodiment of a method 900 for measuring the color of a target, according to the present invention. The method 900 may be implemented by the system 700 illustrated in FIG. 7, operating in conjunction with a software application that executes at the image capturing device and/or a wirelessly coupled remote computing device. As such, reference is made in the discussion of the method 900 to various components of the system 700. It will be appreciated, however, that operation of the method 900 is not limited to the configuration of the system 700. For example, the method 900 may alternatively be implemented by the system 1100 in FIG. 11.

The method 900 starts in step 902.

In step 904, the system 700 is placed on a flat horizontal surface with the imaging port 710 facing down (i.e., spaced apart from the flat horizontal surface).

In optional step 906 (illustrated in phantom), the software application is launched on the imaging capturing device 720, and the lens 716 is aimed through the imaging port 710. An illuminance map (W) is captured by the image capturing device 720 by using the flash 718 to capture an image of the cap. If the illuminance map was captured within a threshold period of time (e.g., a few hours or days), step 906 can be skipped.

In step 908, the system 700 is positioned between the image capturing device 720 and the target 730. For instance, the system 700 is assembled and positioned relatively to the image capturing device 720 and the target 730 as illustrated in FIG. 7. At this point, the cap is removed from the sample port 708, and the plate 712 carrying the reference colors 704 is positioned as illustrated in FIG. 7.

In step 910, the image capturing device 720 (or a remote computer communicating wirelessly with the image capturing device 720) freezes all of the camera settings of the image capturing device 720 to predetermined values. The frozen settings include, for example, exposure time and white balance.

In step 912, the image capturing device 720 captures a plurality of images of the target 730 using the flash 718.

In optional step 914 (illustrated in phantom), the image capturing device 720 (or a remote computer communicating wirelessly with the image capturing device 720) normalizes each of the plurality of images with the corresponding illumination map (W). Step 914 may be omitted depending on the actual illumination uniformity.

In step 916, the image capturing device 720 (or a remote computer communicating wirelessly with the image capturing device 720) constructs first and second matrices. The first matrix is a 3×K matrix (referred to as "D"), where K is the number of reference colors 704. The first matrix D contains the red, green, and blue (RGB) values of the reference colors 704 under the illuminant, as extracted from each of the plurality of images. The second matrix is a P×K matrix (referred to as $R_T$), where P is the number of data points in each spectrum. The second matrix $R_T$ contains the reflectance spectra of the reference colors 704.

In step 918, the image capturing device 720 is calibrated using the matrices. In one embodiment, calibration is performed by first estimating a third, P×3 matrix (referred to as "M") and an offset P-vector (b) that map (as closely as possible) the camera RGB matrix (referred to as "D") to the corresponding reflectance matrix $R_T$. This mapping may be expressed as discussed above in EQN. 1, or as the homogenous equation expressed by EQN. 2, where $M_A$=[M b] is the P×4 matrix comprising M right-augmented by the column vector b, and $D_A$=[D' 1']' is the 4×K matrix comprising D augmented from the bottom by a row K-vector 1 of ones.

Here, D' is the transpose of D. $M_A$ may again be estimated using the least square approximation expressed above in EQN. 3.

In step 920, the image capturing device 720 (or a remote computer communicating wirelessly with the image capturing device 720) estimates the reflectance of the target 730. In one embodiment, an estimated reflectance P-vector (referred to as "r") can be computed for each pixel of the target 730 from its measured camera 4 vector $d_A$ (i.e., the column vector d extended by a one at the end) as expressed above in EQN. 4.

The average reflectance ($\overline{d_A}$) of the target 730 can be further estimated by averaging the reflectances ($d_A$) of all of the pixels that belong to the target 730. Then, the color tristimulus values of the target 730 can be further calculated from the average reflectance, the predefined illuminant, and CIE color matching functions.

In step 922, the image capturing device 720 (or a remote computer communicating wirelessly with the image capturing device 720) identifies at least one stored color that is believed to match the color of the target 730. In one embodiment, the image capturing device 720 searches a color database containing a large pool of standard colors and suggests at least a predefined number (e.g., three) of those colors that exhibit a smallest color difference relative to the estimated tristimulus values of the target 730. The identified colors may be displayed to a user (e.g., on a screen of the image capturing device 720) and/or stored for future reference.

In optional step 924 (illustrated in phantom), the image capturing device 720 (or a remote computer communicating wirelessly with the image capturing device 720) measures the glossiness of the target 730. Estimating the glossiness will further refine the selection of a matching color. In one embodiment, the glossiness is estimated as "matte," "semi-gloss," or "glossy." The glossiness may be measured by removing the gloss trap 714 and repeating steps 910-920. A more quantitative assessment of glossiness can be made by pre-calibrating the gloss assessment against samples whose glossiness is known.

The method 900 ends in step 926.

Figure 10:
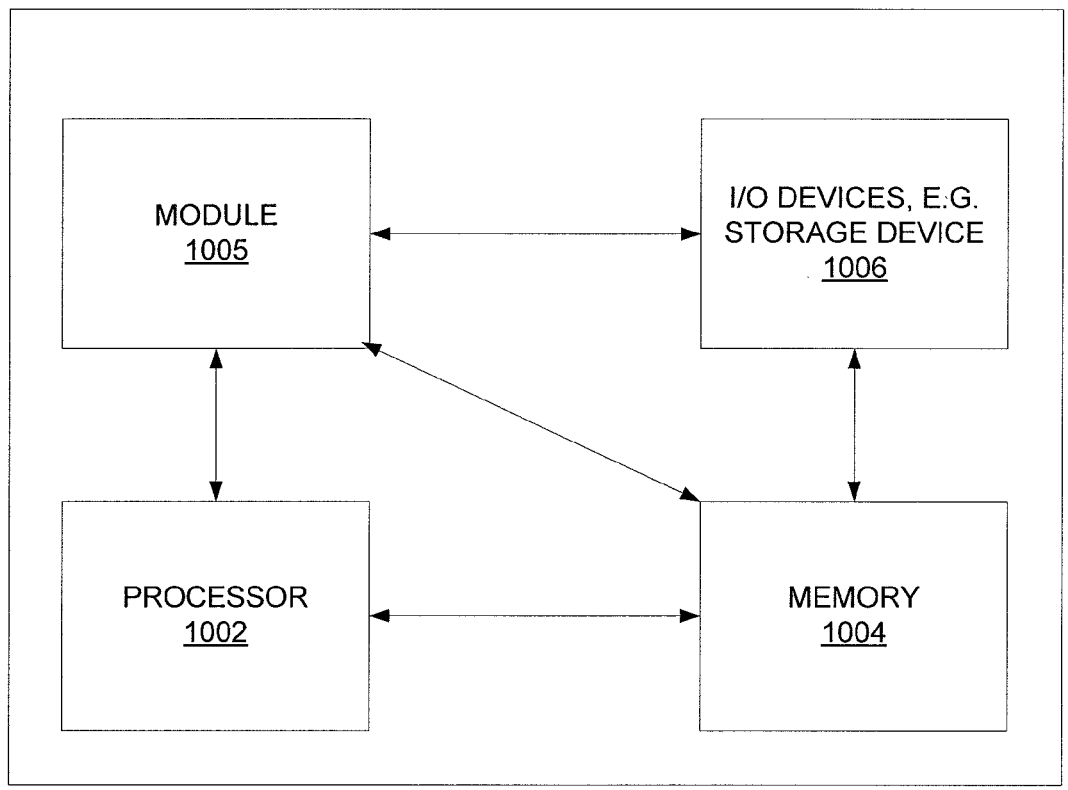
FIG. 10 is a high-level block diagram of the present invention that is implemented using a general purpose computing device.

FIG. 10 is a high-level block diagram of the present invention that is implemented using a general purpose computing device 1000. The general purpose computing device 1000 may comprise, for example, part of a smart phone having an integrated color camera. Alternatively, the general purpose computing device 1000 may be part of a computing device that is wirelessly coupled to a smart phone. In one embodiment, a general purpose computing device 1000 comprises a processor 1002, a memory 1004, an measurement module 1005 and various input/output (I/O) devices 1006 such as a display, a keyboard, a mouse, a stylus, a wireless network access card, an image capturing device, and the like. In one embodiment, at least one I/O device is a storage device (e.g., a disk drive, an optical disk drive, a floppy disk drive). It should be understood that the measurement module 1005 can be implemented as a physical device or subsystem that is coupled to a processor through a communication channel.

Alternatively, as discussed above, the measurement module 1005 can be represented by one or more software applications (or even a combination of software and hardware, e.g., using Application Specific Integrated Circuits (ASIC)), where the software is loaded from a storage medium (e.g., I/O devices 1006) and operated by the processor 1002 in the memory 1004 of the general purpose computing device 1000. Thus, in one embodiment, the measurement module 1005 for image-based color measurement as described herein with reference to the preceding Figures, can be stored on a computer readable storage device (e.g., RAM, magnetic or optical drive or diskette, and the like).

It should be noted that although not explicitly specified, one or more steps of the methods described herein may include a storing, displaying and/or outputting step as required for a particular application. In other words, any data, records, fields, and/or intermediate results discussed in the methods can be stored, displayed, and/or outputted to another device as required for a particular application. Furthermore, steps or blocks in the accompanying Figures that recite a determining operation or involve a decision, do not necessarily require that both branches of the determining operation be practiced. In other words, one of the branches of the determining operation can be deemed as an optional step.

While the foregoing is directed to embodiments of the present invention, other and further embodiments of the invention may be devised without departing from the basic scope thereof. Various embodiments presented herein, or portions thereof, may be combined to create further embodiments. Furthermore, terms such as top, side, bottom, front, back, and the like are relative or positional terms and are used with respect to the exemplary embodiments illustrated in the Figures, and as such these terms may be interchangeable.

What is claimed is:

1. An apparatus for assisting in measuring a color of a target, the apparatus comprising:
   an enclosed housing having a first aperture formed in a first end and a second aperture formed in an opposite second end and aligned concentrically with the first aperture;
   an array of light emitting diodes positioned inside the housing, between the first aperture and the second aperture; and
   an array of reference colors having known reflectance spectra, the array of reference colors being removably positioned inside the housing, between the array of light emitting diodes and the second aperture.

2. The apparatus of claim 1, wherein the apparatus is configured for removable attachment to an image capturing device at the first end.

3. The apparatus of claim 1, further comprising:
   a lens having a short focal length and positioned in the housing between the array of light emitting diodes and the first aperture.

4. The apparatus of claim 1, wherein the array of light emitting diodes comprises a plurality of light emitting diodes arranged in a ring.

5. The apparatus of claim 1, wherein the array of light emitting diodes comprises a plurality of light emitting diodes each positioned to illuminate the second aperture at an angle of approximately forty-five degrees.

6. The apparatus of claim 1, wherein the array of light emitting diodes comprises a plurality of light emitting diodes of different spectral types.

7. The apparatus of claim 6, wherein the different spectral types include narrow-band spectra having peak wavelengths that cover a visual range from approximately four hundred nanometers to approximately seven hundred nanometers.

8. The apparatus of claim 7, wherein the different spectral types further include a broad-band white spectrum.

9. The apparatus of claim 1, wherein the array of reference colors comprises a plurality of swatches of different colors arranged in a ring.

10. The apparatus of claim 1, further comprising:
    a single light emitting diode positioned between the array of light emitting diodes and the array of reference colors; and a photodiode positioned between the array of light emitting diodes and the array of reference colors, on an opposite side of the housing from the single light emitting diode.

11. A system for measuring a color of a target, the system comprising:
an image capturing device for capturing an image of the target;
an apparatus detachably coupled to the image capturing device, the apparatus comprising:
an enclosed housing having a first aperture formed in a first end and a second aperture formed in an opposite second end, wherein a lens of the image capturing device is aligned concentrically with the first aperture and the second aperture, such that the second aperture is positioned approximately at a center of a field of view of the image capturing device;
an array of light emitting diodes positioned inside the housing, between the first aperture and the second aperture; and
an array of reference colors having known reflectance spectra, the array of reference colors being removably positioned inside the housing, between the array of light emitting diodes and the second aperture; and
a processor for processing the image of the target to estimate the color.

12. The system of claim 11, wherein the image capturing device is a color camera integrated in a smart phone.

13. The system of claim 12, wherein the processor is integrated in the smart phone.

14. The system of claim 11, wherein the processor is wirelessly coupled to the smart phone.

15. The system of claim 11, further comprising:
an auxiliary lens having a short focal length and positioned in the housing between the array of light emitting diodes and the first aperture.

16. An apparatus for assisting in measuring a color of a target, the apparatus comprising:
an integrating sphere;
a sample port formed in the integrating sphere;
an imaging port formed in the integrating sphere, on an opposite side of the integrating sphere from the sample port;
a light source port formed in the integrating sphere, near the imaging port, for coupling light emitted from outside of the integrating sphere into the integrating sphere; and
an array of reference colors having known reflectance spectra, the array of reference colors being arranged on a ring that is positioned at the sample port.

17. The apparatus of claim 16, wherein the ring is removably positioned at the sample port.

18. The apparatus of claim 16, wherein the imaging port comprises:
an auxiliary lens having a short focal length; and
an opening for an image capturing device to capture an image of the target.

19. A method for measuring a color of a target, the method comprising:
capturing a plurality of images, each of the plurality of images depicting a plurality of reference colors and at least a portion of the target, wherein reflectance spectra of the plurality of reference colors is known, wherein each of the plurality of images is captured under a known illuminant;
estimating an average reflectance of the target in accordance with the plurality of images; and
calculating color tristimulus values of the target in accordance with the average reflectance, the known illuminant, and color matching functions,
wherein the capturing, the estimating, and the calculating are all performed by a computing device including an integrated color camera.

20. The method of claim 19, wherein the computing device is a smart phone.

21. The method of claim 19, wherein the known illuminant is provided by a flash of the color camera.

22. The method of claim 19, wherein the known illuminant is provided by a plurality of light emitting diodes positioned between the integrated color camera and the target.

23. The method of claim 22, wherein the plurality of light emitting diodes includes light emitting diodes of different spectral types.

24. A non-transitory computer readable storage device containing an executable program for measuring a color of a target, where the program performs steps comprising: capturing a plurality of images, each of the plurality of images depicting a plurality of reference colors and at least a portion of the target, wherein reflectance spectra of the plurality of reference colors is known, wherein each of the plurality of images is captured under a known illuminant; estimating an average reflectance of the target in accordance with the plurality of images; and calculating color tristimulus values of the target in accordance with the average reflectance, the known illuminant, and color matching functions, wherein the computer readable storage device is part of a computing device including an integrated color camera.

* * * * *